United States Patent
Luo et al.

(10) Patent No.: US 6,365,147 B1
(45) Date of Patent: Apr. 2, 2002

(54) METHODS FOR REMOVING ENDOTOXINS FROM BIOLOGICAL SOLUTIONS USING IMMOBILIZED METAL AFFINITY CHROMATOGRAPHY

(75) Inventors: Robert Gang Luo, Edison; Yun Kang, Harrison, both of NJ (US)

(73) Assignee: New Jersey Institute of Technology, Newark, NJ (US)

( * ) Notice: Subject to any disclaimer, the term of this patent is extended or adjusted under 35 U.S.C. 154(b) by 0 days.

(21) Appl. No.: 09/416,934

(22) Filed: Oct. 13, 1999

(51) Int. Cl.$^7$ .............................................. A01N 63/00
(52) U.S. Cl. ..................... 424/93.1; 604/5.02; 210/661; 210/670; 210/691; 210/692
(58) Field of Search .............................. 514/2; 210/692, 210/661, 670, 691; 424/93.1; 604/5.02

(56) References Cited

U.S. PATENT DOCUMENTS 5,476,715 A * 12/1995 Otto ........................... 428/407

FOREIGN PATENT DOCUMENTS

JP          02-193913     *  7/1990

OTHER PUBLICATIONS

Holmes, "Immobilized Iron(III) Metal Affinity Chromatography for the Separation of Phosphorylated Macromolecules: Ligands and Applications", J. Liq. Chrom. & Rel. Technol. 20 (1): 123–142 (1997).*
Aida et al., 1990, Removal of endotoxin from protein solutions by phase separation using Triton X–114, J. Immunological Methods 132:191–5.
Andersson et al., 1986, Isolation of Phosphoproteins by Immobilized Metal ($Fe^{3+}$) Affinity Chromatography, Analytical Biochem. 154:250–4.
Belanich et al., 1996, Reduction of Endotoxin in a Protein Mixture Using Strong Anion–Exchange Membrane Absorption, Pharmaceutical Technology, Mar. 1998, 142–5.
Guo et al., 1997, Removal of Endotoxin from Aqueous Solutions by Affinity Membrane, Biomedical Chromatography 11:164–6.
Hirayama et al., 1994, Cross–linked N,N–dimethylaminopropylacrylamide spherical particles for selective removal of endotoxin, J Chromatography A 676:267–75.
Hou et al., 1990, Endotoxin Removal by Anion–Exchange Polymeric Matrix, Biotechnology and Applied Biochem. 12:315–24.
Issekutz et al., 1983, Removal of Gram–Negative Endotoxin from Solutions by Affinity Chromatography, J Immunological Methods 61:275–81.
Kang et al., 1998, Chromatographic removal of endotoxin from hemoglobin preparations. Effects of solution conditions on endotoxin removal efficiency and protein recovery, J Chromatography A 809:13–20.

Kang et al., 1999, Accurate chromogenic measurement of endotoxin concentration in a hemoglobin–lipopolysaccharide complex solution, Am. Biotechnol. Lab 17:30 and 32.
Karplus et al., 1987, A new method for reduction of endotoxin contamination from protein solutions, J Immunological Methods 105:211–220.
Legallais et al., 1997, Strategies for the depyrogenation of contaminated immunoglobulin G solutions by histidine–immobilized hollow fiber membrane, J Chromatography B 691:33–41.
Li et al., 1999, Quantitative Determination of $Ca^{2+}$ Effects on Endotoxin Removal and Protein Yield in a Two–Stage Ultrafiltration Process, Separation Science and Technology 34(9):1729–41.
Li et al., 1998, Use of $Ca^{2+}$ to re–aggregate lipopolysaccharide (LPS) in hemoglobin solutions and the subsequent removal of endotoxin by ultrafiltration, Biotechnology Techniques 12:119–122.
Matsumae et al., 1990, Specific Removal of Endotoxin from Protein Solutions by Immobilized Histidine, Biotechnology and Applied Biochem. 12P:129–40.
Muszynska et al., 1992, Model studies on iron(III) ion affinity chromatography. II. Interaction of immobilized iron(III) ions with phosphorylated amino acids, peptides and proteins, J. Chromatography. 604:19–28.
Patel et al., 1998, Protein absorption dissociation constants in various types of biochromatography, Absorption and its Applications in Industry and Environmental Protection Studies in Surface Science and Catalysis, 120:829.
Petsch et al., 1997, Membrane adsorbers for selective removal of bacterial endotoxin, J Chromatography B, 693:79–91.
Scopes, 1987,Immobilized Metal Affinity Chromatography (IMAC), in Protein Purification, Third Edition, Cantor, Charles R. (ed), Springer–Verlag, New York, pp. 183–185.
Scopes et al., 1994, Immobilized Metal Affinity Chromatography, in Protein purification: principles and practice, Third Edition, Cantor, Charles R. (ed), Springer–Verlag New York, Inc., pp. 180–182.
Sulkowski, 1985, Purification of proteins by IMAC, Trends in Biotech. 3(1):1–7.
Tant et al, 1992, Biomat., Art. Cells & Immob. Biotech., 20(2–4), 457–62.
Yip et al., 1994, Immobilized Metal Ion Affinity Chromatography, Molecular Biotech. 1:151–164.

* cited by examiner

*Primary Examiner*—Sandra E. Saucier (57) ABSTRACT

The present invention relates to methods for depleting endotoxin from biological solutions by exposure of solutions containing endotoxin to an immobilized metal affinity chromatography matrix composed of a metal ion such as iron (III) bounds to a resin, wherein the metal is capable of selectively binding endotoxin in the solution. These methods are useful for purifying, for example, biological products prepared using bacterial cells, or products in which bacterial contamination is problematic. In another embodiment, endotoxin in circulation in a body can be removed by exposing the blood to the aforementioned matrix, whereby endotoxin is removed before the blood is returned to the body.

12 Claims, 4 Drawing Sheets

METHODS FOR REMOVING ENDOTOXINS FROM BIOLOGICAL SOLUTIONS USING IMMOBILIZED METAL AFFINITY CHROMATOGRAPHY

FIELD OF THE INVENTION

The invention relates to methods for the purification of biological solutions by removal of endotoxin, including the ex-vivo depletion of endotoxin from blood.

BACKGROUND OF THE INVENTION

Bacterial endotoxins are lipopolysaccharides (LPS) derived from the outer cell membranes of Gram-positive and Gram-negative bacteria (Vaara and Nikaido, 1984). Endotoxins are known to have potent biological effects in human. Serious endotoxin infection can cause sepsis and septic shock, leading to severe hypertension, cardiovascular collapse, multiple organ failure and death (Billiau and Vandekerckhove, 1991). In biotechnology industry, bacteria are widely used to produce recombinant DNA products such as peptides and proteins. Bacterial endotoxins have been recognized by the industry as a major cause of the pyrogenic reactions that can be encountered during the administration of biotherapeutics (Hou and Zaniewski, 1990). The removal of these physiologically active agents from final bioproducts has always been a challenge, especially in the situations where endotoxins bind product proteins. Significant product loss and low product yield can result from the separation steps employed to remove endotoxins.

Although numerous methods such as ion exchange adsorption (Webber et al., 1995), ion exchange membrane (Belanich et al., 1996), ion-exchange filter (Hou and Zaniewski, 1990), ultrafiltration (Li and Luo, 1998, 1999), extraction (Aida and Pabst, 1990) have been studied for endotoxin removal from protein solutions, affinity adsorption has proven to be the most effective technique. Polymyxin B has been investigated intensively as an endotoxin binding ligand since Issekutz (1983) reported its ability to remove endotoxin from solutions. In subsequent studies, polymyxin B has been immobilized on chromatographic supports such as Sepharose (Karprus et al., 1987) to remove endotoxin from protein solutions. Membrane (Petsch et al., 1997) or fiber (Tani et al., 1992) have been used as the support as well. Immobilized histidine has also been employed to remove endotoxin from protein solutions. Sepharose resin (Matsumae et al., 1990), filter-paper (Guo et al., 1997), and hollow fiber membrane (Legallais et al., 1997) have been used as the support. Hirayama et al. (1994) studied the use of cross-linked N,N-dimethylaminopropylacrylamide (DMAPAA) spherical particles for selective removal of endotoxin from protein solutions. They found that ionic strength had less effect on the endotoxin removal efficiency with DMAPAA than with immobilized histidine. An ACTICLEAN ETOX affinity column from Sterogene Bioseparations (Carlsbad, Calif.) has been used to remove endotoxin from hemoglobin preparations where the protein formed complex with LPS subunits (Kang and Luo, 1998). The effects of various solutions such as endotoxin-free water, NaCl and $CaCl_2$ on the endotoxin removal efficiency and protein recovery in the chromatographic process were investigated.

Immobilized metal affinity chromatography (IMAC, also know as metal chelate chromatography) was introduced as a new technique for protein purification by Porath et al. in 1975. Since then IMAC has gained wide acceptance in purification of proteins and peptides (Sulkowski, 1985; Yip and Hutchens, 1994; Scopes, 1994). Much of the earlier work concentrated on using $Cu^{2-}$ or $Zn^{2+}$ as the chelating metal ion (Sulkowski, 1985; Scopes, 1987). Later $Fe^{3+}$ was found to be a very effective chelating ion for isolation of phosphorylated amino acids, peptides and proteins based on the preferential affinity between the immobilized iron (III) ion and the phosphate groups in the biomolecules (Andersson and Porath, 1986; Muszynska et al., 1992).

Numerous methods and devices have been described for the extracorporeal (ex vivo) removal or treatment of various blood components by circulating blood outside of the body through an apparatus containing membranes or particulate supports to which are attached binding agents for the component to be removed. For example, heparinase has been attached to a particulate support to degrade heparin in blood U.S. Pat. No. 4,373,023); chelants to remove metal ion oxidants have been described for the treatment of atherosclerosis (U.S. Pat. No. 5,753,227); and an adsorbent for removing low density lipoprotein (LDL) and endotoxins (U.S. Pat. No. 5,476,715), the endotoxin bound using a homo-, co-, or terpolymer of acrylic acid and/or methacrylic acid.

It is towards the development of improved methods for depleting endotoxin from biological and other solutions that the present invention is directed.

The citation of any reference herein should not be construed as an admission that such reference is available as "Prior Art" to the instant application.

SUMMARY OF THE INVENTION

In its broadest aspect, the present invention is directed to a method for depleting endotoxin from a solution comprising the steps of: (1) providing an immobilized metal affinity chromatography matrix comprising a metal ion; (2) exposing the solution to the matrix under conditions wherein the endotoxin contained therein binds to the matrix; and (3) collecting the solution after exposure to the matrix, wherein the solution is depleted of endotoxin. Various adsorbent materials or matrices may be used for the aforementioned purpose, in the form of beads, fibers, or other formats, comprising, by way of non-limiting example, various plastic resins such as polystyrene, polymers such as poly (hydroxymethacrylate), agarose, and the like. The metal binding or chelating moiety of the matrix may be, for example, iminodiacetic acid, nitrilotriacetic acid or tris (carboxymethyl)ethylenediamine. These moieties bind a metal ligand. Metal ions (metal ligands) useful for this purpose include but are not limited to iron (III), copper (II), cobalt (II), nickel (II), zinc (II), cerium (III), magnesium (II), calcium (II), chromium (III), lanthanum (III), lutetium (III), scandium (III), thallium (III), ytterbium (III), thorium (IV), and uranate (II). Iron (III) is preferred.

In one embodiment of the invention, in step (3) above the matrix is exposed to an elution buffer to elute material other than endotoxin that has bound to the matrix. The elution buffer may be by way of a non-limiting example, a phosphate buffer, and may be present at a concentration of about 0.02 M to about 0.06 M. In another embodiment of the invention, the matrix is provided in the form of a column, the solution to be depleted of endotoxin is passed through said column, and subsequently the column is washed with a buffer to collect material not adhered to said matrix. Proteins that may adhere to the matrix may be eluted with an elution buffer which displaces the proteins but does not release endotoxin. The elution buffer may be, for example, a phosphate buffer, and may be present at a concentration of about 0.02 M to about 0.06 M. In yet a further embodiment, the solution to be depleted of endotoxin is adjusted such that upon exposure to the aforementioned matrix, endotoxin is selectively bound to the matrix but proteins are not. Such adjustment may be provided using phosphate, such as a phosphate buffer, in the solution. A concentration of phosphate of about 0.02 M to about 0.06 M achieves this purpose, although this may be varied within the scope of the invention. In a further example of the practice of the invention, the matrix may be regenerated after use by treatment with a solution of a metal chelator to remove the metal and endotoxin bound thereto, followed by washing and recharging with metal ion. A non-limiting of a metal chelator useful for this purpose may include but is not limited to ethylenediaminetetraacetic acid (EDTA); ethylene glycol-bis(beta-aminoethyl ether)-N,N,N',N'-tetraacetic acid (EGTA); ethylenediamine-N,N'-diacetic acid (EDDA); or nitrilotriacetic acid (NTA).

In another broad aspect of the invention, a method is provided for the extracorporeal depletion of endotoxin from the circulation in a patient. In this method, the patient's blood is exposed ex vivo to an immobilized metal affinity chromatography matrix comprising a metal ion as described hereinabove, wherein endotoxin in the blood is bound by the matrix, and the blood is subsequently returned to the patient's circulation.

These and other aspects of the present invention will be better appreciated by reference to the following drawings and Detailed Description.

BRIEF DESCRIPTION OF THE DRAWINGS

FIG. 3 Protein elution profile of BSA-LPS mixture from the IMAC column. A: Chromatogram of UV response at 280 nm, recorded by the data acquisition system. B: Chromatogram of Bradford assay results of fractions and fraction pools. (1) Loading period: feed, 10 ml mixture containing 16.14 μg/ml BSA and 18.26 EU/ml LPS; flow rate, 1 ml/min. (2) Washing period: 20 ml buffer A at 2 ml/min. (3) Elution period, 10 ml buffer B at 1 ml/min. (4) Elution period, 22 ml buffer C at 1 min/ml.

FIG. 4 Protein elution profile of HbAo-LPS mixture from the IMAC column. A: Chromatogram of UV response at 280 nm, recorded by the data acquisition system. B: Chromatogram of Bradford assay results of fractions and fraction pools. (1) Loading period: feed, 10 ml mixture containing 19.06 μg/ml BSA and 21.26 EU/mi LPS; flow rate, 1 ml/min. (2) Washing period: 20 ml buffer A at 2 ml/min. (3) Elution period, 22 ml buffer C at 1 ml/min.

DETAILED DESCRIPTION OF THE INVENTION

The inventors herein have discovered the utility of immobilized metal affinity chromatography for the depletion of endotoxin from solutions, and in particular, biological solutions. As noted above, removal of endotoxin from pharmaceutical products is a critical step in the preparation or manufacture of safe medicaments for human and other animal administration. Medicaments, in particular those prepared from materials of bacterial origin, such as recombinant proteins and other molecules, nucleic acids, including plasmid DNA molecules, such as for gene therapy and for antisense nucleic acid therapy, are particularly in need of purification of the expressed products from bacterial cell wall materials. Furthermore, manufacturing processes for biological materials in which growth of microorganisms occurs within the materials during the manufacturing process are also important candidates for the depletion or removal of endotoxin before packaging for human administration. The foregoing examples are merely illustrative of the types of biological solutions that are in need of processing to remove contaminating endotoxin before they can be used for human administration, whether at the manufacturing stage, or at the early experimental or clinical trial stage.

In another example, the blood of an individual in need of depletion of endotoxin levels represents another biological solution from which endotoxin depletion may be carried out in accordance with the present invention.

The foregoing discussion provides examples of biological solutions from which endotoxin depletion is desired. The present invention provides new methods for depleting endotoxin from such biological solutions while minimally removing other components. The method involves generally the use of materials and processes related to immobilized metal affinity chromatography (IMAC), which the present inventors have found provides a surprising and remarkable ability to specifically bind endotoxin from solution. Although IMAC is described in further detail herein, the method of the invention may be achieved using any suitable matrix, resin, resin beads, fibers, membranes, particulate materials, adsorbent material, or solid support (collectively referred to herein as the matrix or the stationary phase) on which a metal ion capable of binding endotoxin may be affixed and retain its endotoxin-binding activity. As described previously (Porath et al., 1975; Sulkowski, 1985; Yip and Hutchens, 1994; Scopes, 1994), IMAC, also known as metal chelate chromatography, comprises an affinity separation medium in which a metal ion is bound to a stationary phase, providing exposure of the metal ion to interact with and bind molecules to which it adheres. Various stationary phases have been used for IMAC, including plastics and biological polymers such as, but not limited to, agarose, polystyrene, and poly(hydroxymethacrylate). Other suitable particulate supports materials include styrene divinylbenzene copolymer, cross-linked dextran, polyhydroxy ethyl methacrylate, polyacrylamide, cellulose, polyurethane, and derivatives of the foregoing, such as cellulose acetate. Various degrees of cross-linking of the foregoing polymers may impart desired characteristics.

As will be noted in more detail below, the aforementioned matrices are specific for binding endotoxin and bind endotoxin with high affinity, but may bind other components from a biological solution, such as proteins. In carrying out the depletion of endotoxin from a biological solution, two general procedures may be followed. In one procedure, the matrix is first allowed to bind endotoxin and any other components that may bind under the conditions provided during this binding step. In a subsequent step, the matrix is washed with a solution that elutes the other components from the matrix, such as proteins, but does not elute endotoxin. One non-limiting example of conditions under which elution of bound components other than endotoxin is accomplished is by the use of a phosphate buffer. The separation thus may be achieved by, for example, carrying out the binding step in the presence of acetate buffer, and then eluting other bound components using phosphate buffer. A concentration of phosphate of about 0.02 M to 0.06 M achieves this objective, although this can be varied within the scope of the invention, and an appropriate phosphate concentration can be determined readily by the skilled artisan. In another example, the binding step may be carried out in the presence of phosphate buffer, wherein endotoxin is bound to the matrix but binding of other components such as proteins does not occur. Other buffers in addition to phosphate are suitable, i.e., those which are capable of binding to the metal ion on the matrix more strongly than to proteins, and thus are capable of eluting the protein or preventing the proteins from binding, but do not affecting the binding of endotoxin to the metal ion on the matrix. Furthermore, the pH of the buffer should be selected such that it does not cause the bound metal ion to be displaced from the matrix; typically for such matrices, a pH of less than 8 is suitable, and is usually less than about 7, and usually no lower than pH 3.5. The pH of the buffer in the examples is 5.5. The selection of the pH may also be guided by any possible sensitivity of the solution and its components to pH. These examples are merely illustrative of the conditions and procedures which may be employed to take advantage of the finding herein of the specific binding of endotoxin by the aforementioned matrices. The particular operating conditions, types, amounts and compositions of biological solutions, relative reduction in endotoxin desired, and other factors to guide the skilled artisan in selecting the procedure most appropriate and cost-effective in carrying out the separation or, for example, tailoring it to existing bioprocess facilities. Furthermore, the concentration of phosphate to achieve the optimal elution of the bound components other than endotoxin, within the tolerance of the particular system for phosphate, is readily determinable by the skilled artisan, as is the concentration of phosphate to include in the solution if the selective removal of endotoxin is desired.

Non-limiting examples of useful moieties which bind the metal and is covalently bound to the stationary phase include iminoacetate (IDA), 2-hydroxy-3[N-(2-pyridylmethyl) glycine]propyl, nitrilotriacetic acid, and tris(carboxymethyl) ethylenediamine. Such stationary phases and bound moieties for binding the metal ions are known in the art, and the foregoing examples are merely exemplary of suitable metal ion binding moieties. Iminodiacetate, also known as iminodiacetic acid, is a preferred moiety.

Metals which may bind to the IMAC matrix for use in the present invention include, but are not limited to, iron (III), copper (II), cobalt (II), nickel (II), zinc (II), cerium (III), magnesium (II), calcium (II), chromium (III), lanthanum (III), lutetium (III), scandium (III), thallium (III), ytterbium (III), thorium (IV), and uranate (II). As noted in the art, the metal and the corresponding moiety on the stationary phase are selected to provide the desired properties of the matrix. Procedures for the selection of the appropriate combination is well within the realm of the skilled artisan. In a preferred embodiment of the present invention, the moiety on the stationary phase is iminoacetic acid, and the metal is iron (III), also referred to as ferric ion or $Fe^{+3}$. Although the above-described examples of other metals are useful for the present purposes, commonly-available and inexpensive metal ions such as iron (III) are preferred solely from a practical perspective.

Preparation of the matrix and charging with the appropriate metal ion may be accomplished as guided by the art. Numerous such materials are commercially available. For instance, as used in the Examples herein, a SEPHAROSE High Performance metal chelating resin consisting of highly cross-linked agarose beads to which iminodiacetic acid is coupled by stable ether bonds via a seven-atom spacer was purchased from Pharmacia. Such material has a metal ion binding capacity of about 23 $\mu$mol Cu(II) per ml of matrix. In other examples, Sigma Chemical Co. provides an iminoacetic acid cross-linked via amino groups to epoxy activated 4% beaded agarose, using a 12 atom spacer. This material has a binding capacity of 30–40 $\mu$mol $CuSO_4$ per ml of matrix. Another commercially available material is iminodiacetic acid bound to macroreticular polystyrene beads (16–50 mesh; AMBERLITE IRC-718), with a binding capacity of 1.1 meq per ml. Other commercially available products include CHELEX resin, in particular CHELEX 100 which is an iminodiacetic acid-modified polystyrene bead material, and DIAION CR11, a similar material. The skilled artisan, in selecting the appropriate matrix or resin for the uses intended herein, can determine from the endotoxin level in the solution, the amount of solution to be processed, and the available equipment, the amount of matrix or resin needed for efficient purification of the sample. As will be further noted below, an advantage of the invention is that the above-described matrix can be easily regenerated and reused.

The following discussion is merely an example of the invention on a small scale. The skilled artisan can readily scale up or down the components to suit their particular needs. As separation methodology is a well developed art, many variations in the procedures described here are embraced by the present invention. In the examples herein, a column format is used; however, other modes of treating the solution with the endotoxin-binding support phase is embraced herein, including but not limited to exposure in a batch treatment method, in which the support phase in particulate form is added to the solution, mixed, and then separated therefrom; and an in-line filter in which a solution containing endotoxin is passed from one stage of manufacturing to the next. As described previously, the particular operating conditions to provide either selective depletion of endotoxin during passage of the biological solution, that is, in the presence of, for example, phosphate buffer, or the sequential steps of binding and then elution of bound components other than endotoxin from the matrix, will be governed by the desired degree of endotoxin removal to be achieved as well as the bioprocess conditions, nature and amount of the biological solution, and other parameters around which the process of the invention operates. It will be readily apparent to the skilled artisan how to design the operating particulars to be compatible with the conditions and goals. As noted above, the concentration of phosphate and the nature of the buffer can be readily determined by the skilled artisan to conform the objects of the invention to the particular process for which endotoxin depletion is desired, such as the concentration of the elution buffer of the concentration of phosphate to include directly in the biological solution for the selective depletion of endotoxin. Variations in these parameters are fully embraced in the invention.

In utilizing any one of the previously described or related resins for the purposes of the invention, a separation may be carried out using the resin in a column format. For example, on a small scale, a 0.7×2.5 cm column may be filled with the aforementioned matrix. After washing the matrix, it is charged by passage therethrough of a solution containing the metal ion to be bound; for example, a solution of ferric chloride may be used to charge an aforementioned column with iron (III) ions. Before use, the column is then washed to remove any unbound metal ions.

To deplete endotoxin from a solution, the solution is passed through the column to expose the endotoxin in the solution to the bound metal ions, to which endotoxin binds. The solution and its non-binding components pass through the column and are collected. The solution retained in the dead space in the column can be flushed out with an appropriate buffer. The capacity of the column, the flow rates, pressure, and other parameters used for column separations will be taken into account to maximize the efficiency of the separation and producing a product with levels of endotoxin reduced to below a target level.

As noted above, under certain conditions such as in the presence of phosphate buffer, selective binding of endotoxin to the matrix occurs. In the absence of such conditions, binding of endotoxin occurs together with other components, the other components can be later eluted by exposing the matrix to phosphate buffer, for example. Either of these methods may be used to take advantage of the findings disclosed herein. An advantage of the selective binding in the presence of, for example, phosphate buffer, is that endotoxin removal can be achieved in a flow-through arrangement, such as an in-line filter in a bioprocess manufacturing line, or in an extracorporeal device to remove endotoxin from blood. In the alternate process, comprising a binding step and an eluting step, this process may be suitable for large-scale processing of manufactures materials and when the column may be treated for reuse. A further advantage of the latter method, as noted in the Examples below, is that any components that are bound and subsequently eluted may be concentrated in the eluate, which may be an advantage in the purification and concentration of certain endotoxin-depleted materials. As noted above, these and other variations in the employment of the matrix herein to take advantage of its selective endotoxin binding capacity are embraced by the present invention, and as noted above, a skilled artisan may employ the invention in any one of many arrangements.

As mentioned above, certain IMAC matrices as described herein after binding endotoxin can be regenerated and reused. In this procedure, the matrix is exposed to a reagent which strips off the metal ion under conditions which does not damage the matrix. In one example, a solution of a metal-binding compound such as ethylenediaminetetraacetic acid (EDTA) is washed through the column, which removed the iron (III) and any endotoxin bound thereto. After subsequent washing, the column may be recharged with iron (III).

As will be noted in the examples herein, the binding strength of the matrices described herein for endotoxin is significantly greater than for protein or other components found in various biological solutions; thus, the endotoxin is specifically removed. The eluate may be pooled, and used for subsequent steps in processing.

In summary, the method of the invention for depleting endotoxin from a biological sample comprises the steps of (1) providing an immobilized metal affinity chromatography matrix comprising a metal ion; (2) exposing the solution to the matrix, wherein the endotoxin binds; and (3) collecting the solution after exposure to the matrix, the solution depleted of endotoxin. As noted above, numerous variations are possible on this scheme. The collection step may include elution of components other than endotoxin which bind to the matrix. The means of exposure of the solution to the matrix may take the form of any number of suitable configurations; the column described above being a mere example. The matrix may be regenerated afterwards by stripping the metal ion using a soluble metal chelator, and after its removal, recharging the matrix with metal ion.

Another aspect of the invention is directed to the therapeutic use of the endotoxin-binding matrix of the invention for the removal of endotoxin from the body. As mentioned above, serious and often fatal consequences accompany systemic exposure of the body to bacteria and bacterial products. In the instance of septic shock and toxic shock, bacterial products entering the circulation induce the production by white blood cells and other cell types of a variety of factors that lead to profound organ and system dysfunction and failure. These include hyperdynamic circulation, hypotension, decreased systemic vascular resistance, pyrexia and increased oxygen dependency. Patients with sepsis, prone to sepsis or who are exposed to conditions that may lead to the development of sepsis are candidates for the removal of endotoxin from circulation. Such candidates include victims of wounds to the gut, such as knife or gunshot wounds; patients undergoing surgical procedures in which exposure to bacteria in the form of intestinal contents may occur, such as gut surgery, and appendectomy, among others.

As noted above in the Background section, it is known in the art to circulate blood from an individual through an apparatus or device for treatment and then return the treated blood back to the individual. In fact, numerous membranes and particulate supports bearing moieties to either capture components from the blood or enzymes to act on circulating components have been used. Apparatuses and membrane or particulate supports are known which are biocompatible and provide for the treatment of an individual without introducing toxic or other harmful agents to body, nor damaging the blood or its components, for example by activating cells or factors, as they pass through the device.

In one embodiment of this aspect of the invention, the blood of the individual from which endotoxin removal is desired is directed out of the body and circulated ex vivo through an endotoxin binding matrix of the invention and then back into the body. Such matrices have been described above for depleting endotoxin from biological solutions; such matrices may also be prepared for in vivo use. Such matrices must of course be nontoxic and not release toxic components into the blood, not induce any adverse effects on the individual. As numerous extracorporeal blood cleansing and other devices have been described in the art as noted above, the in-vivo-compatible matrices of the invention are modifications therein in which the metal ion is available on the resin for binding endotoxin from circulation.

As will be shown in the examples below, an elution study of bovine serum albumin (BSA) or hemoglobin Ao (HbAo) and endotoxin (ET) mixture by 0.06 M $NaH_2PO_4$ was investigated. More than 90% protein yield and more than 99% endotoxin removal were achieved in product solutions. After the chromatographic process, most of the ET was removed from the protein solution. The BSA was concentrated by 4.7 times and HbAo 1.9 times. This method has many advantages over the traditional endotoxin removal methods, especially affinity chromatography method. First, traditional affinity chromatography can not disrupt the endotoxin-protein complex. Since the affinity between the metal and endotoxin is very high, it is possible to disrupt the protein-endotoxin complex. Second, endotoxin removal efficiency in some traditional methods was affected by ionic strength. As the ion strength is more than 0.2 M, it is very difficult to achieve satisfactory endotoxin removal results.

Utilizing the IMAC procedure at 1.0 M ionic strength, the endotoxin removal efficiency is not affected. Finally, the column regeneration of traditional affinity column is very time consuming and most of them require the use of NaOH, as described further below. For the IMAC column, after each run, it may treated by use of a stripping buffer to remove adsorbed molecules and metal ion. Then, before each use it is charged with the new metal ion. The whole process is very simple and rapid.

In addition to its high endotoxin removal efficiency and protein yield, an IMAC column has an important advantage in the column cleaning procedure over immobilized polymyxin B, histidine and other affinity columns used for endotoxin removal in the prior art, due to one of IMAC's unique features. In the affinity chromatographic processes mentioned above, endotoxin in the protein-LPS mixture is preferentially adsorbed by the ligand and it stays in the column even after the elution step. In order to make the column ready for the next cycle, the endotoxin in the column must be removed. In processes where immobilized polymyxin B, histidine and other affinity ligands are used, the endotoxin is removed by a cleaning-in-place (CIP) step, which usually involves applying concentrated NaOH (e.g., 1.0 M) to the column, sometimes for a long period of time (e.g., overnight, Kang and Luo, 1997). In an IMAC column, the adsorbed endotoxin can be easily removed by applying a stripping agent such as EDTA in a routine stripping step. The stripping step can be performed in a short period of time, for example, about an hour. The stripping agent strips the metal ion as well as the endotoxin from the column. Other stripping agents capable of removing the metal ion from its binding moiety may be used. No concentrated NaOH is required, unless it is used for sanitation purposes. Moreover, due to its versatility, an IMAC column may be employed as an endotoxin removal column at one time and as a protein separation column at another time after cleaning, while different metal ions and elution buffers are used respectively.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE 1

Endotoxin Elution Profile

The experimental system for the studies disclosed herein is as follows.

Experimental Apparatus.

The experiments were conducted using a GRADIFRAC chromatographic system (Amersham Pharmacia Biotech, Piscataway, N.J.). Feed and mobile phase solutions were transferred by an adjustable peristaltic P-1 pump. The ultraviolet absorbance of the eluent from the column was measured by a UV-1 monitor. The operating wavelength was 280 nm. The flow cell used in the monitor was a standard cell with an optical path length of 1.00 cm. The experimental results were recorded by two means. The first one was a REC 102 2-channel recorder, which was used to show chromatograms directly during the experiments. The second one was a data acquisition system M1101 (Keithley Metrabyte, Cleveland, Ohio) incorporated with a computer, which was used to record the chromatograms in digital forms so that they could be transferred later for data processing and analysis. A GRADIFRAC fraction collector was used to collect fractions for protein and endotoxin assay.

IMAC Column and Adsorbent Resin

A 0.7×2.5 cm HITRAP Chelating column was purchased from Amersham Pharmacia Biotech. The column was packed with Pharmacia chelating SEPHAROSE High Performance resin consisting of highly cross-linked agarose beads to which iminodiacetic acid (IDA) was coupled by stable ether bounds via a seven-atom spacer arm. The mean diameter of the adsorbent particle is approximately 34 mm.

Buffers

All protein-LPS mixtures were prepared in buffer A—0.5 M NaCl in 0.02 M acetate buffer at pH 5.5. Four buffer reservoirs were used in the chromatographic operation. The starting buffer was buffer A. The first elution buffer, buffer B, was 0.5 M $NH_4Cl$ in 0.02 M acetate buffer at pH 5.5. The second elution buffer, buffer C, was 0.06 M $NaH_2PO4$ in buffer A. The stripping buffer, buffer D, was 0.05 M EDTA (ethylenediaminetetraacetic acid) in buffer A. All buffers were filtered by a 0.22 mm filter and degassed by vacuum for at least 25 min prior to being applied to the column.

Endotoxin, Proteins and Other Materials

Endotoxin from *Escherichia coli* 026:B6 (Sigma Chemical Co., St. Louis, Mo.) was used in all experiments. Hemoglobin Ao (HbAo, ferrous), bovine serum albumin (BSA), $FeCl_3$, NaCl, $NaH_2PO_4$, $NH_4Cl$ and EDTA were also purchased from Sigma. All solution transfers were performed by endotoxin free devices. Sterile, disposable plasticware was used at all times to prevent endotoxin contamination. All solutions were prepared with MILLI-Q water generated by a BIOCEL water purification system (Millipore Corporation, Bedford, Mass.). The endotoxin concentration in the MILLI-Q water was below 0.05 EU/ml based on the results of LAL tests in our laboratory.

Column Preparation and Operation

The HITRAP Chelating column was stored in 20% ethanol when purchased. The column was first washed with 5 ml MILLI-Q water at a flow rate of 1 ml/min to remove the ethanol. Then the column was loaded with 0.5 ml of 0.1 M $FeCl_3$ solution at 1 ml/min to charge $Fe^{3+}$ to the resin. Finally, the column was washed with 5 ml MILLI-Q water at 1 ml/min to replace the unbound $Fe^{3+}$ from solution. The column was now charged with metal ion and ready for use. Before applying the feed, a blank run was performed to elute unspecifically bound metal ions that might otherwise be eluted during the desorption. The column was washed with 2.5 ml of buffer A at 2 ml/min followed by 5 ml of buffer B at 1 ml/min. The column was then equilibrated with 2.5 ml of buffer A at 1 ml/min. The feed (10 ml of protein-LPS mixture) was applied to the column at 1 ml /min. The column was then washed with the starting buffer (buffer A) at 2 ml/min for 10 min. Finally, the column was eluted by buffer B and/or buffer C at 1 ml/min using step gradients. The column was regenerated by washing with buffer D to strip all the metal ions, followed by washing with 5 ml of MILLI-Q water, both at a flow rate of 1 ml/min.

Protein Assay

Protein concentrations in eluents of the column were measured by two means. First, the ultraviolet absorbance of the eluents was monitored continuously at 280 nm for protein peaks. Second, fractions were collected and all fractions or fractions polls were assayed for protein concentration using Bradford method (Bradford, 1976).

Endotoxin Assay

To determine endotoxin concentration, a chromogenic Limulus amebocyte lysate (LAL) test kit QCL-1000 from BioWhittaker (BioWhittaker Inc., Walkersville, Md.) with a modified procedure was used. The sensitivity of this test is 0.01 EU/ml. The reaction mixtures were measured at 405 nm by a Hitachi U-2000 spectrophotometer (Hitachi Instruments Inc., Danbury, Conn.) and the results were compared to a standard curve to obtain endotoxin concentrations. However, HbAo also has a strong absorbance at 405 nm and deduction of HbAo absorbance is necessary. The correction was done by deducting the HbAo absorbance from total absorbance of the reaction mixture (Kang and Luo, 1999).

Endotoxin Removal From BSA-LPS Mixture

BSA solution prepared with buffer A was spiked with endotoxin. The concentrations of protein and endotoxin in this feed solution were determined by Bradford and LAL assay, respectively. 10 ml of the feed solution was loaded to the column at 1 ml/min and the fraction collection started at the beginning of the loading. The subsequent washing and elution steps were described in the "Column preparation and operation" section. The fraction collection program was set in the following fashion. Both features of "fraction collection" and "peak collection" of the GRADIFRAC system were used. The fractions were collected at every 5 min before the last "peak collection" was activated. The fractions were collected at every 1 min after the last "peak collection" was finished. Both buffer B and C were used to elute the protein while the endotoxin was kept in the column. There were total 20 fractions collected from the beginning of the loading to the end of the elution. All fractions or fraction pools were assayed for protein and endotoxin concentrations.

Endotoxin Removal From HbAo-LPS Mixture

HbAo prepared with buffer A was spiked with endotoxin. The concentrations of protein and endotoxin in this feed solution were determined by Bradford and LAL assay, respectively. 10 ml of the feed solution was loaded to the column at 1 ml/min and the fraction collection started at the beginning of the loading. The subsequent washing and elution steps were described in the "Column preparation and operation" section. Buffer C was used to elute the protein while the endotoxin was kept in the column. The fraction collection program was set in the same fashion as mentioned above. There were total 13 fractions collected from the beginning of the loading to the end of the elution. All fractions or fraction pools were assayed for protein and endotoxin concentrations.

Figure 1:
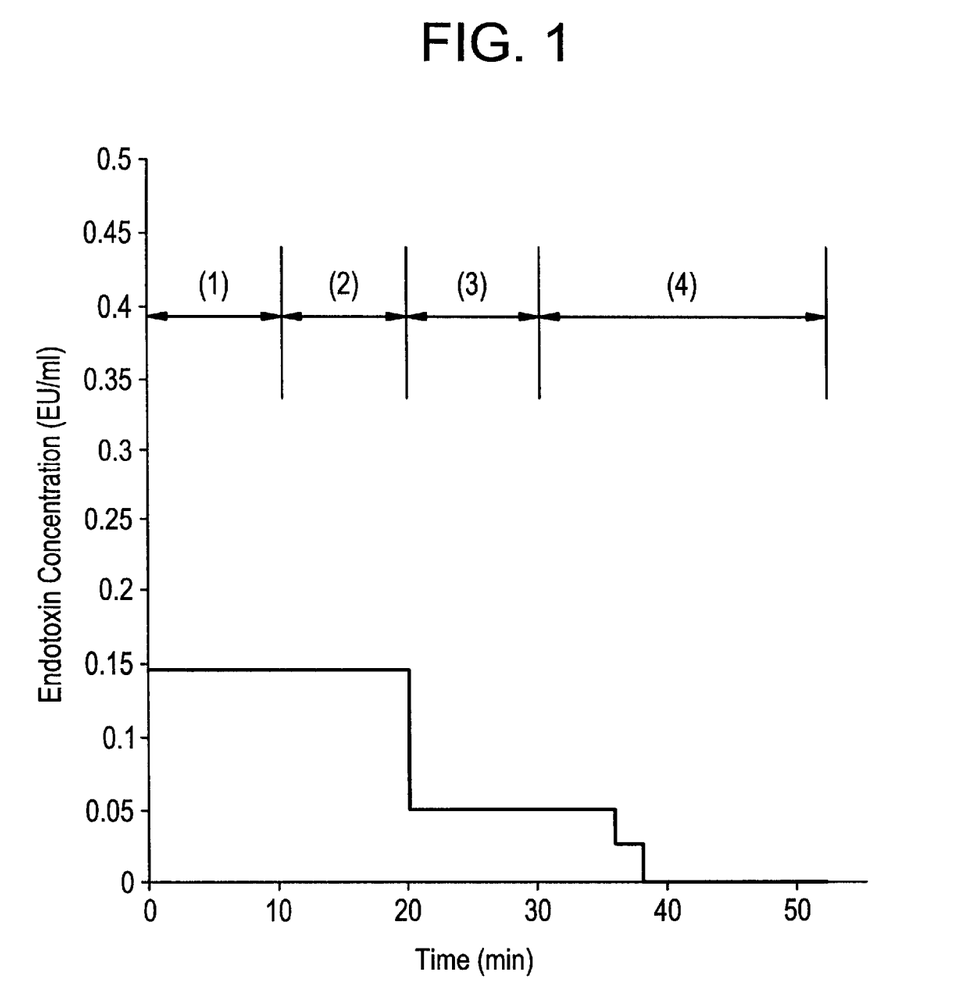
FIG. 1 Endotoxin elution profile of BSA-LPS mixture from the IMAC column. (1) Loading period: feed, 10 ml mixture containing 16.14 μg/ml BSA and 18.26 EU/ml LPS; flow rate, 1 ml/min. (2) Washing period: 20 ml buffer A at 2 ml/min. (3) Elution period, 10 ml buffer B at 1 ml/min. (4) Elution period, 22 ml buffer C at 1 ml/min.
Figure 2:
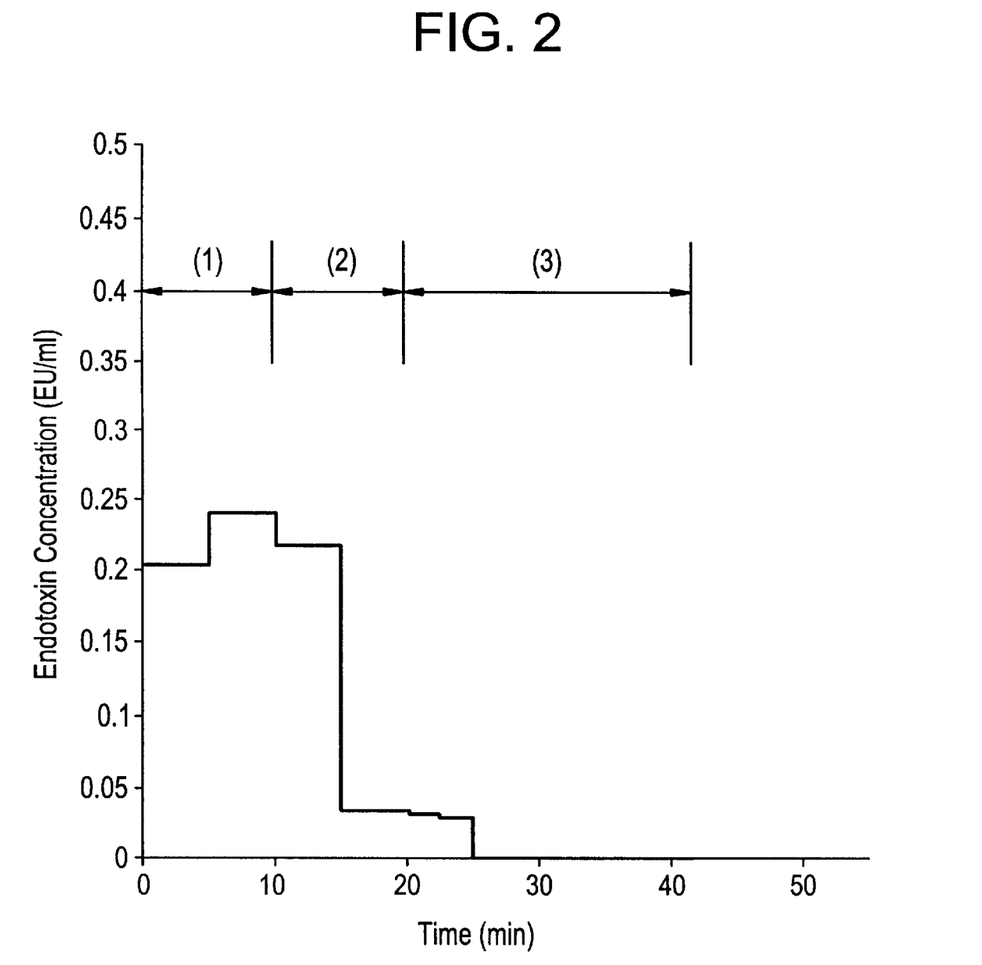
FIG. 2 Endotoxin elution profile of HbAo-LPS mixture from the IMAC column. (1) Loading period: feed, 10 ml mixture containing 19.06 μg/ml BSA and 21.26 EU/ml LPS; flow rate, 1 ml/min. (2) Washing period: 20 ml buffer A at 2 ml/min. (3) Elution period, 22 ml buffer C at 1 ml/min.

FIG. 1 shows the elution profile of endotoxin in BSA-LPS mixture separated by the IMAC column. It can be seen that endotoxin concentrations in all fractions were very low. During the loading period (0 to 10 min) and the washing period (10 to 20 min), the output endotoxin concentration was 0.15 EU/ml. During the elution period (20 to 52 min) while the protein was eluted out, the output endotoxin concentration was 0.05 EU/mi before 36 min and 0.03 EU/mi from 36 to 38 min. After 38 min, the endotoxin contents were below the detection level of the LAL test. FIG. 2 shows the elution profile of endotoxin in HbAo-LPS mixture separated by the IMAC column. Similar to the situation in FIG. 1, endotoxin concentrations were very low during the loading period (0–10 min), the washing period (10–20 min) and the elution period (20–42).

EXAMPLE 2

Endotoxin Removal Efficiency of Protein-LPS Mixtures by the Column

The endotoxin removal ability of this process was quantitatively evaluated using three parameters: Local Endotoxin Removal Efficiency, LERE; Global Endotoxin Removal Efficiency, GERE; and Endotoxin Log Reduction, ELR. Local Endotoxin Removal Efficiency, LERE.

LERE was determined by the following equation (Li and Luo, 1999):

$$LERE=(m_{lps}^{feed}-m_{lps}^{peak})/m_{lps}^{feed} \qquad (1)$$

Where $m_{lps}^{feed}$ is the amount of endotoxin (in endotoxin unit, EU) in the feed loaded on the column, and $m_{lps}^{peak}$ is the amount of endotoxin (EU) in the protein peak collected.

Global Endotoxin Removal Efficiency, GERE, was determined by the following equation:

$$GERE=(m_{lps}^{frac})/(m_{lps}^{feed}+m_{lps}^{buffer})$$

Where $m_{lps}^{buffer}$ is the amount of endotoxin (EU) in all buffer solutions used to wash and elute the column, $m_{lps}^{frac}$ is the amount of endotoxin (EU) in all fractions collected.

Endotoxin Log Reduction, ELR, was determined by the following equation:

$$ELR=\log(m_{lps}^{feed})/(m_{lps}^{feed})$$

LERE, GERE, and ELR were calculated based on endotoxin concentrations in the feeds, buffers and fractions of chromatographic runs for BSA-LPS and HbAo-LPS mixtures. The data was summarized in Table 1. When BSA-LPS mixture was used as the feed, the GERE was 97.5%, which means 97.5% of the total amount of endotoxin input (in the feed and all buffer solutions) was retained by the column. The LERE was 99.7%, which means only 0.3% of the endotoxin content in the feed was eluted out with the protein peak. High endotoxin log reduction was also obtained. Similarly, LERE, GERE, and ELR for HbAo-LPS separation were all very high as shown in Table 1.

Figure 3A:
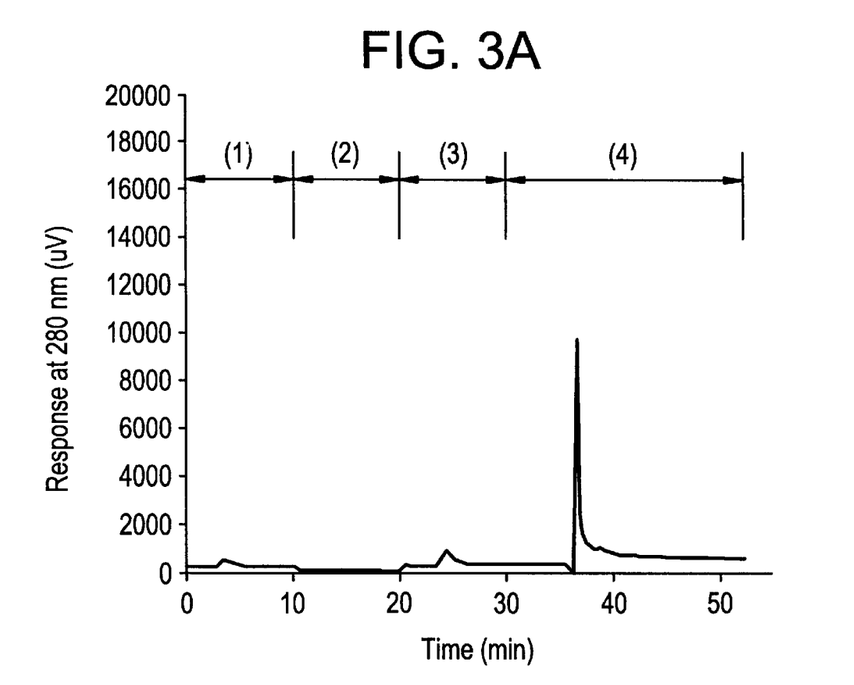
Figure 3B:
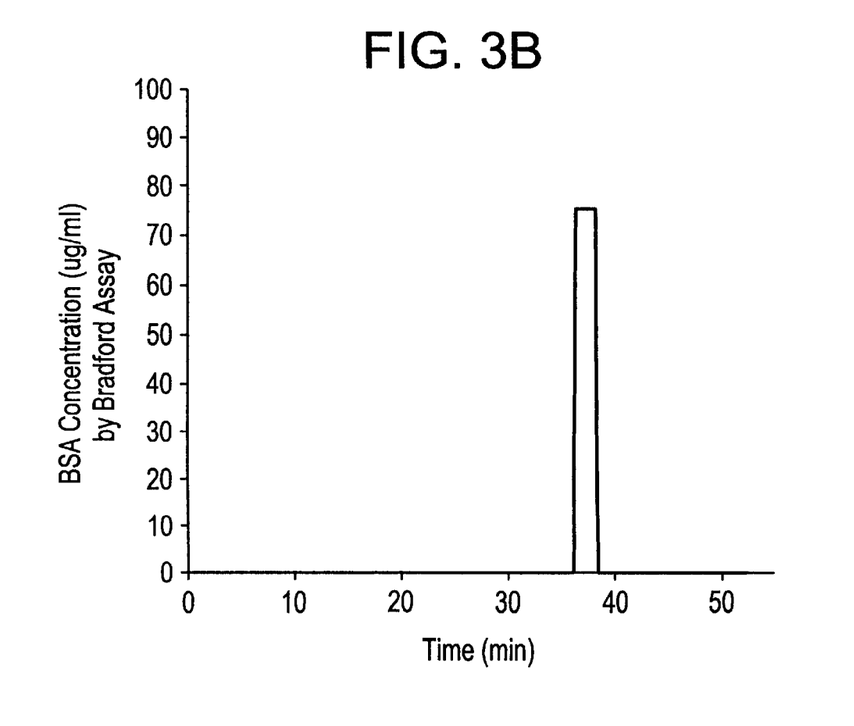
Figure 4A:
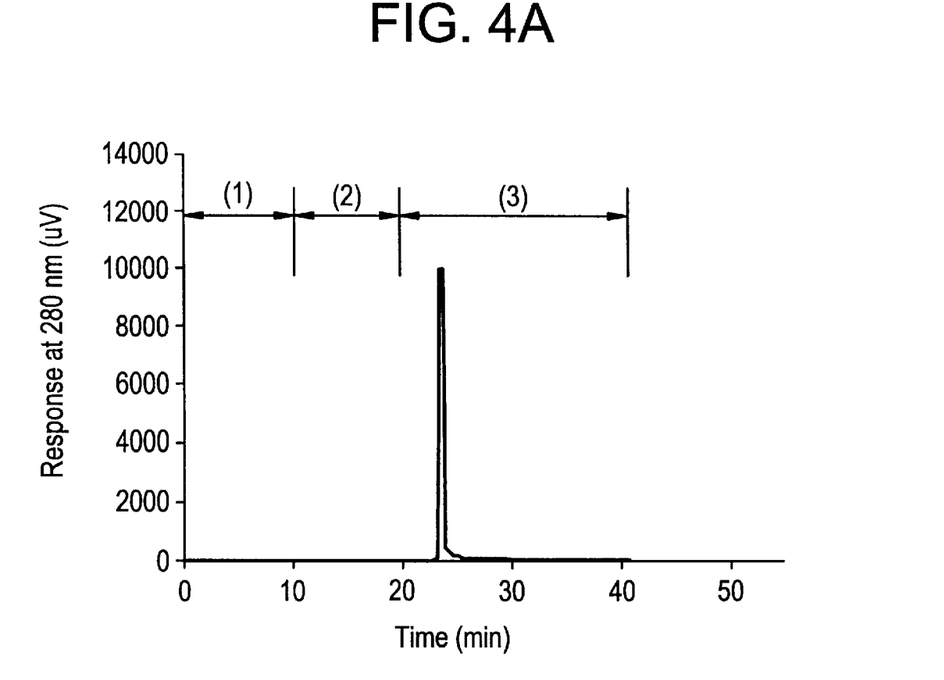
Figure 4B:
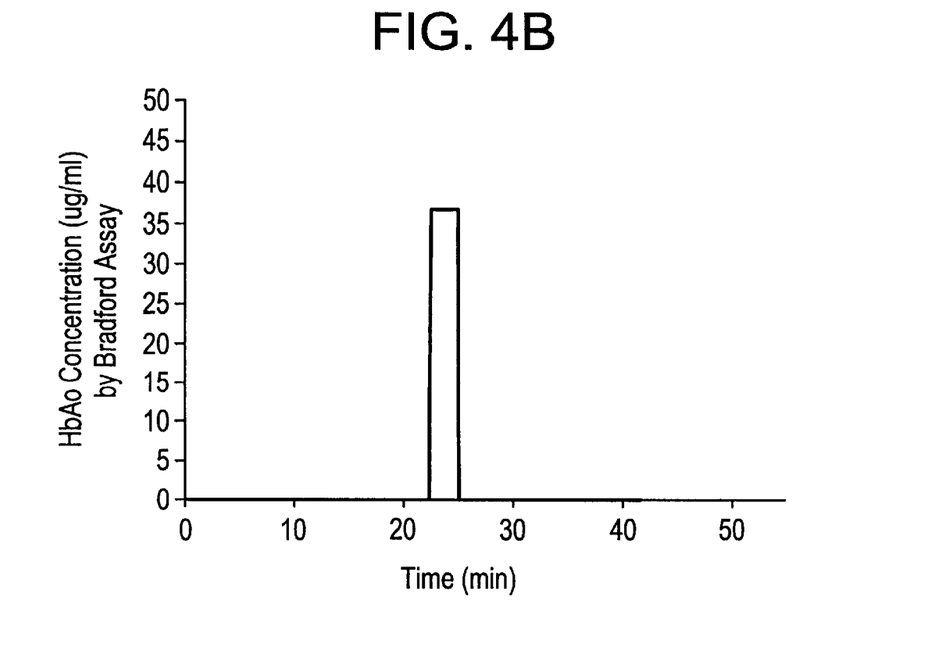

FIG. 3 shows the elution profile of BSA in the BSA-LPS mixture separated by the IMAC column. The chromatogram in FIG. 3A was recorded directly by the data acquisition system, and the elution profile in FIG. 3B was obtained by Bradford assay of fractions and fraction pools. It can be seen that the BSA peak came out at around 36 min. The peak was sharp with a concentration of 75.31 µg/ml. During the loading (0 to 10 min), washing (10 to 20 min) and early elution (20 to 36 min) periods, the baseline of the chromatogram was very stable except a small peak at 24 min. The Bradford assay result of the corresponding fraction of this peak showed no protein content. FIG. 4 shows the elution profile of HbAo in the HbAo-LPS mixture separated by the IMAC. A sharp HbAo peak came out at around 24 min with a concentration of 36.56 µg/ml. Similar to the situation in the BSA-LPS experiment, the baseline of the HbAo chromatogram was also very stable during the loading (0 to 10 min), washing (10 to 20 min) and the early elution (20 to 24 min) periods.

Protein Yield of Protein-LPS Mixtures by the Column

Protein yield, Y, of the IMAC process was determined by the following equation:

$$Y=(m_{pro}^{feed})/(m_{lps}^{feed}).$$

Where $m_{pro}^{peak}$ is the amount of protein (µg) in the feed loaded on the column, and $m_{pro}^{peak}$ is the amount of protein (µg) in the protein peak collected. For an endotoxin-removing step in downstream bioprocessing, it is ideal to have both high endotoxin removal efficiency and high protein yield. We have summarized the endotoxin removal and protein yield data of the two protein-LPS mixtures in Table 1. When BSA-LPS mixture was used as the feed, the protein yield was 93.3%. When HbAo-LPS mixture was used as the feed, the protein yield was 95.7%. We also noticed that the BSA concentration in the product fraction pool was 75.31 µg/ml, which was 4.7 times of the BSA concentration in the feed. The HbAo concentration in the product fraction pool was 36.56 μg/ml, which was 1.9 times of the BSA concentration in the feed.

TABLE 1

Local endotoxin removal efficiency, LERE, global endotoxin removal efficiency, GERE, endotoxin log reduction, ELR, and protein yield, Y, of the IMAC process

| Feed | LERE (%) | GERE (%) | ELR | Y (%) |
|---|---|---|---|---|
| BSA-LPS mixture | 99.7 | 97.5 | 2.56 | 93.3 |
| HbAo-LPS mixture | 99.9 | 97.7 | 3.17 | 95.9 |

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

Aida, Y., and M. J. Pabst, "Removal of Endotoxin from Protein Solutions by Phase Separation using X-114," *J. Immunol. Meth.*, 132, 191 (1990).

Andersson, L., and J. Porath, "Isolation of Phosphoproteins by Immobilized Metal ($Fe^{3+}$) Affinity Chromatography," *Anal. Biochem.*, 154, 250 (1986).

Belanich, M., B. Cummings, D. Grob, J. Klein, A. O'Connor, and D. Yarosh, "Reduction of Endotoxin in a Protein Mixture Using Strong Anion-Exchange Membrane Absorption," *Pharm. Tech.*, 20, 142 (1996).

Billiau, A., and F. Vandekerckhove, "Cytokines and Their Interactions with Other Inflammatory Mediators in the Pathogenesis of Sepsis and Septic Shock," *Eur. J Clin. Invest.*, 21, 559 (1991).

Bradford, M. M., "A Rapid and Sensitive Method for the Quantitation of Microgram Quantities of Protein Utilizing the Principles of Protein-dye Binding," *Anal Biochem.*, 72, 248 (1976).

Guo, W., Z. Shang, Y. Yu, and L. Zhou, "Removal of Endotoxin from Aqueous Solutions by Affinity Membrane," *Biomedical Chromatogr.*, 11, 164 (1997).

Hirayama, C., T. Sakata, Y. Yugawa, and H. Ihara, "Cross-linked N, -dimethylaminopropylacrylamide Spherical Particles for Selective Removal of Endotoxin," *J. Chromatogr. A*, 676, 267 (1994).

Hou, K., and R. Zaniewski, "Endotoxin Removal by Anion-Exchange Polymeric Matrix," *Biotechnol Appl. Biochem.*, 12, 315 (1990).

Issekutz, A. C., "Removal of Gram-Negative Endotoxin from Solutions by Affinity Chromatography,", *J. Immunol. Meth.*, 61, 275 (1983).

Kang, Y., and, R. G. Luo, "Chromatographic Removal of Endotoxin from Hemoglobin Preparations: Effects of Solution Conditions on Endotoxin Removal Efficiency and Protein Recovery," *J. Chromatogr. A*, 809, 13 (1998).

Kang, Y., and R. G. Luo, "Accurate Chromogenic Measurement of Endotoxin Concentration in A Hemoglobin-Lipopolysaccharide Complex Solution," *Amer. Biotech Lab.*, in press (1999).

Karprus, T. E., R. J. Ulevitch, and C. B. Wilson, "A New Method for Reduction of Endotoxin Contamination from Protein Solutions," *J. Immunol. Meth*. 105, 221 (1987).

Legallais, C., F. B. Anspach, S. M. A. Bueno, K. Haupt, and M. A. Vijayalakshima, "Strategies for the Depyrogenation of Contaminated Immunoglobulin G Solutions by Histidine-immobilized Hollow Fiber Membrane," *J. Chromatogr. B*, 691, 33 (1997).

Li, L. , and R. G. Luo, "Quantitative Determination of $Ca^{+2}$ Effects on Endotoxin Removal and Protein Yield in A Two-stage Ultrafiltration Process," *Separation Sci. and Tech.*, in press (1999).

Li, L., and R. G. Luo, "Use of $Ca^{+2}$ to Re-aggregate Lipopolysaccharide (LPS) in Hemoglobin Solutions and the Subsequent Removal of Endotoxin by Ultrafiltration," *Biotechnol. Tech.*, 12, 119 (1998)

Matsumae, H., S. Minobe, K. Kindan, T. Watanabe, T. Sato, and T. Tosa, "Specific Removal of Endotoxin from Protein Solutions by Immobilized Histidine," *Biotechnol Appl. Biochem.*, 12, 129 (1990).

Muszynska, G., G. Dobrowolsa, A. Medin, P. Ekman, and J. O. Porath, "Model Studies on Iron (III) Ion Affinity Chromatography. II. Interaction of Immobilized Iron (III) Ions with Phosphorylated Amino Acids, Peptides and Proteins," *J. Chromatogr.*, 604, 19 (1992).

Patel, D. C., and R. G. Luo, "Protein Adsorption Dissociation Constants in Various Types of Biochromatography," in *Adsorption and Its Applications in Industry and Environmental Protection*, A. Dabrowski, ed., Vol. 1, 829, Elsevier, Amsterdam (1998)

Petsch, D., T. C. Beeskow, F. B. Anspach, and W. -D. Deckwer, "Membrane Adsorbers for Selective Removal of Bacteria Endotoxin", *J Chromatogr. B*, 693, 79 (1997).

Porath, J., J. Carlsson, I. Olssaon, and G. Belfrage, "Metal Chelate Affinity Chromatography, a New Approach to Protein Fractionation," *Nature*, 258, 598 (1975).

Scopes, R. K., *Protein Purification: Principles and Practice*, Second Ed., Springer-Verlag, New York, p184 (1987).

Scopes, R. K., *Protein Purification: Principles and Practice*, Third Ed., Springer-Verlag, New York, p181 (1994).

Sulkowski, E., "Purification of Proteins by IMAC," *Trends in Biotechnol.*, 3, 1 (1985).

Tani, T., T. M. S. Chang, M. Kodama, and M. Tsuchiya, "Endotoxin Removal from Hemoglobin Solution using Polymyxin B Immobilized Fibre (PMX-F) Followed by a New Turbidometric Endotoxin Assay," *Bioma. Art. Cells & Immob. Biotechnol.*, 20, 457 (1992).

Vaara, M., and H. Nikaido, "Molecular Organization of Bacterial Outer Membrane," in *Handbook of Endotoxin, Vol 1: Chemistry of Endotoxin*, E. T. Rietschel, Ed., Elsevier, New York, p1 (1984).

Weber, C., B. Henne, F. Loth, M. Schoenhofen, and D. Falkenhagen, "Development of Cationically Modified Cellulose Adsorbents for the Removal of Endotoxin," *ASAIO J*, 41, M430 (1995).

Yip, T.-T., and T.W. Hutchens, "Immobilized Metal Ion Affinity Chromatography," *Molecular Biotechnol.*, 1, 151 (1994).

What is claimed is:

1. A method for removing endotoxin from a starting solution containing endotoxin comprising the steps of applying said starting solution to an immobilized metal affinity chromatography matrix comprising iron (III), wherein said endotoxin binds to said matrix; and collecting from said matrix after said exposing a matrix-treated solution, wherein said matrix-treated solution has less endotoxin than said starting solution.

2. The method of claim 1 wherein said immobilized metal affinity chromatography matrix comprises an iron (III) binding moiety selected from the group consisting of imino acetate, 2-hydroxy-3 [N-(2-pyridylmethyl)glycine]propyl, nitrilotriacetic acid, and tris(carboxymethyl) ethylenediamine.

3. The method of claim 1 wherein said matrix is exposed to an elution buffer to elute material other than endotoxin bound to said matrix.

4. The method of claim 3 wherein said elution buffer is a phosphate buffer.

5. The method of claim 4 wherein said phosphate is present at a concentration of about 0.02 M to about 0.06 M.

6. The method of claim 1 wherein said matrix is provided in column form, said solution is passed through said column, and said column is washed to collect material not bound to said matrix.

7. The method of claim 6 wherein in step (c) said matrix is exposed to an elution buffer to elute material other than endotoxin bound to said matrix.

8. The method of claim 7 wherein said elution buffer is a phosphate buffer.

9. The method of claim 8 wherein said phosphate is present at a concentration of about 0.02 M to about 0.06 M.

10. The method of claim 1 wherein said solution comprises an elution buffer wherein endotoxin in said solution selectively binds to said matrix.

11. The method of claim 1 wherein said matrix is regenerated by treatment with a solution of a metal chelator to remove the iron (III) and endotoxin bound thereto, followed by washing and recharging with said iron (III).

12. The method of claim 11 wherein said metal chelator is selected from the group consisting of ethylenediamine-tetraacetic acid; ethylene glycol-bis(beta-aminoethyl ether)-N,N,N',N'-tetraacetic acid; ethylenediamine-N,N'-diacetic acid; and nitrilotriacetic acid.

* * * * *